Nov. 19, 1963 H. B. LEWIS ETAL Plant Pat. 2,311
AZALEA PLANT
Filed Oct. 10, 1962 2 Sheets-Sheet 1
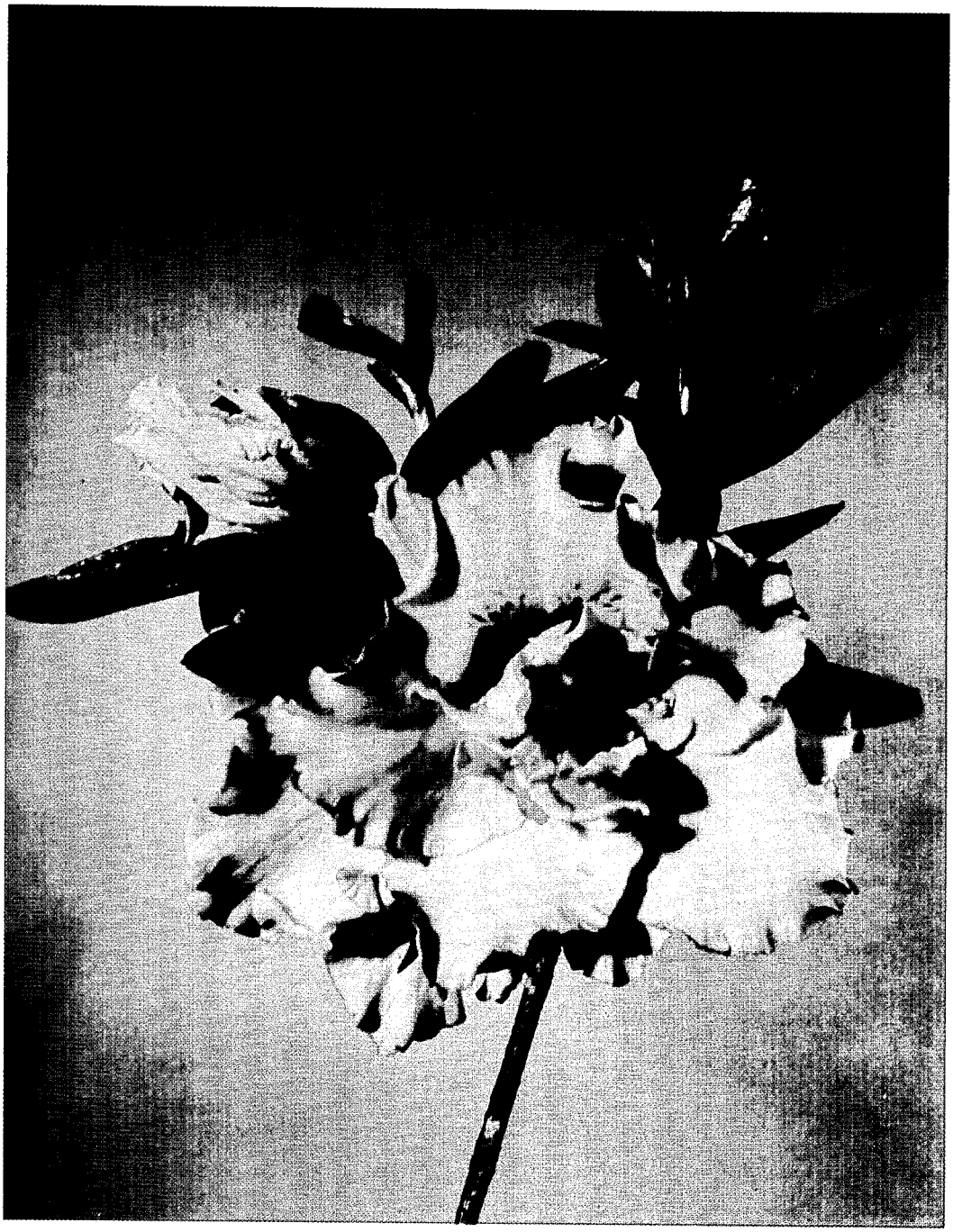
Inventors.
H. B. Lewis and
H. H. Lewis
By: Robb & Robb
Attorneys.

Nov. 19, 1963 H. B. LEWIS ETAL Plant Pat. 2,311
AZALEA PLANT
Filed Oct. 10, 1962 2 Sheets-Sheet 2
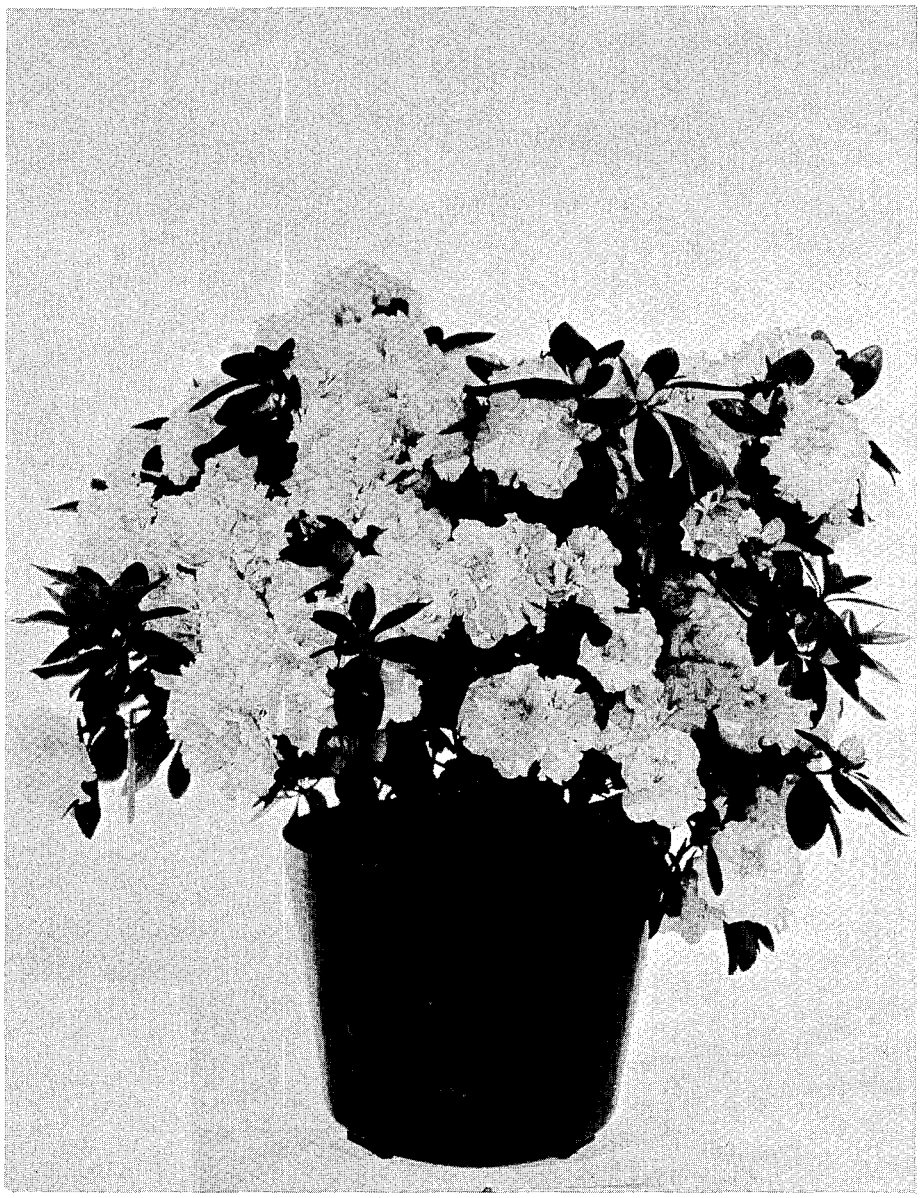
Inventors
H. B. Lewis and
H. H. Lewis
By: Robb & Robb
Attorneys.

United States Patent Office

Plant Pat. 2,311
Patented Nov. 19, 1963

2,311
AZALEA PLANT

Hubert B. Lewis and Helen H. Lewis, both of 16562 E. Leffingwell Road, Whittier, Calif.

Filed Oct. 10, 1962, Ser. No. 229,772
1 Claim. (Cl. Plt.—56)

The present invention relates to a new and distinct variety of azalea plant which was originated by us by crossing the Belgian Indian variety known as "Pink Pearl" (unpatented) with the Rutherfordiana variety known as "L. J. Bobbink" (unpatened), the former being the seed parent and the latter being the pollen parent.

As the result of this breeding, we have produced a new azalea variety which is endowed with a new and improved combination of characteristics, as evidenced by the following features which are outstanding therein and which distinguish the new variety from its parents, as well as from all other varieties of which we are aware:

(1) A compact habit of growth and execptional suitability for forcing;
(2) Attractive glossy green foliage;
(3) Abundant flower production;
(4) A dainty and ruffled flower form;
(5) A distinctive and attractive soft pink general color tonality of the flowers; and
(6) Good keeping qualities of the flowers.

Our new azalea variety does not resemble the pollen parent, "L. J. Bobbink" in any way, but there is some resemblance in flower color only to the flowers of the seed parent, "Pink Pearl." It is a much more compact grower than either parent variety, and its attractive foliage and abundance of very dainty ruffled flowers of soft pink color make the new variety particularly outstanding and distinct from all other varieties.

Asexual reproduction of our new variety by cuttings, as performed at Rivera, California, and at Whittier, California, shows that the foregoing characteristics and distinctions come true to form and are estabilshed and transmitted through succeeding propagations.

The accompanying drawings show a typical specimen plant of our new azalea variety as depicted in black and white to illustrate its general form and habit of growth, as well as typical specimens of the flowers and foliage as depicted in color on a somewhat enlarged scale to better illustrate the details thereof.

The following is a detailed description of our new azalea variety, with color terminology in accordance with the Wilson Horticultural Color Chart, except where general color terms of ordinary dictionary significance are obvious:

Locality where grown and observed: Whittier, California.
Propagation: Holds its distinguishing characteristics through succeeding propagations by cuttings.

*Plant*

Form: Bush; compact.

Habit: Vigorous; medium branching; compact.
Rooting habit: Fair.
Foliage:
*Size.*—Large.
*Quantity.*—Normal.
*Color.*—New foliage: upper side—Scheeles Green, Plate, 860; under side—Spinach Green, Plate 0960/3. Old foliage:upper side—Parsley Green, Plate 00962; under side—Spinach Green, Plate 0960/3.
*Shape.*—Oval; slightly pointed.
*Texture.*—Upper side—glossy. Under side—smooth.
*Margin.*—Smooth.
*Aspect.*—Good.
*Disease resistance.*—Fair resistance to ordinary diseases to which azalea plants are normally subject, as determined by comparison with other varieties grown under the same cultural conditions at Whittier, California.

*Flowers*

Borne: In clusters from multiple buds; on short and stiff stems.
Blooming habit: Very heavy.
Blooming season: Late spring.
Quantity of bloom: Abundant, both outdoors and in greenhouse.
Continuity: One season.
Petalage: 5 petals on each hose under normal conditions, with some dots on each upper hose.
*Color.*—Neyron Rose, Plate 623/2.
*Texture.*—Medium.
*Appearance.*—Inside—most flowers have open center, but a few have a few center petals. Outside—very ruffled.
*Shape.*—From single hose in hose to semi-double hose in hose.
*Arrangement.*—Inner hose offset from outer hose.
Bud: Ruffled. Color—Neyron Rose, Plate 623/2.

*Reproductive Organs*

Stamens: From 4 to 7; some attached to flower petals. Color—white.
Pollen: Abundant. Color—white.
Styles: Well developed.
Ovaries: Normal.

We claim:

A new and distinct variety of azalea plant, substantially as herein shown and described, characterized particularly as to novelty by the unique combination of a compact habit of growth and exceptional suitability for forcing, attractive glossy green foliage, abundant flower production, a dainty and ruffled flower form, a distinctive and attractive soft pink general color tonality of the flowers, and good keeping qualities of the flowers.

No references cited.